US00PP15487P3

(12) United States Plant Patent
Meilland

(10) Patent No.: US PP15,487 P3
(45) Date of Patent: Jan. 25, 2005

(54) SHRUB ROSE PLANT NAMED 'MEIPADAN'

(50) Latin Name: *Rosa hybrida*
Varietal Denomination: Meipadan

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 65 days.

(21) Appl. No.: 10/413,151

(22) Filed: Apr. 15, 2003

(65) Prior Publication Data

US 2004/0210971 P1 Oct. 21, 2004

(51) Int. Cl.[7] ..... A01H 5/00
(52) U.S. Cl. ..... Plt./103
(58) Field of Search ..... Plt./102, 103

(56) References Cited

U.S. PATENT DOCUMENTS

PP9,994 P * 8/1997 Meilland ..... Plt./114

PP11,583 P * 10/2000 Meilland ..... Plt./108

OTHER PUBLICATIONS

HTTP://www.conard–pyle.com/what'snew.htm.*

* cited by examiner

*Primary Examiner*—Bruce R. Campell
*Assistant Examiner*—W C Haas
(74) *Attorney, Agent, or Firm*—Burns, Doane, Swecker & Mathis, LLP

(57) ABSTRACT

A new and distinct variety of Shrub rose plant is provided which abundantly forms on a continuous basis attractive single white blossoms having light fragrance. The plant exhibits a low-growing and mounded growth habit with good vigor. Excellent resistance to Black Spot is displayed. The very dense dark green foliage with a glossy aspect contrasts nicely with the white blossom coloration. The new variety is particularly well suited for growing as attractive ornamentation in the landscape where it serves well as a ground cover.

1 Drawing Sheet

Botanical/commercial classification: *Rosa hybrida*/Shrub Rose Plant.
Varietal denomination: cv. 'Meipadan'.

SUMMARY OF THE INVENTION

The new variety of *Rosa hybrida* Shrub rose plant was created by artificial pollination wherein two parents were crossed which previously had been studied in the hope that they would contribute the desired characteristics. The female parent (i.e., the seed parent) was the 'Meibeluxen' variety (non-patented in the United States). The male parent (i.e., the pollen parent) was 'The Fairy' variety (non-patented in the United States). The parentage of the new variety can be summarized as follows:

'Meibeluxen'×'The Fairy'.

The seeds resulting from the above pollination were sown and small plants were obtained which were physically and biologically different from each other. Selective study resulted in the identification of a single plant of the new variety.

It was found that the new Shrub rose variety of the present invention (a) exhibits a low-growing and mounded growth habit with good vigor, (b) abundantly forms on a continuous basis attractive single white blossoms having light fragrance, (c) forms very dense dark green foliage having a glossy aspect that contrasts well with the white blossom coloration, (d) displays exceptional Black Spot resistance, and (e) is particularly well suited for growing as attractive ornamentation in the landscape.

The new variety well meets the needs of the horticultural industry and can be grown to advantage in parks and gardens where attractive ornamentation is desired. The new variety performs well as a ground cover.

The new variety can be readily distinguished from its ancestors. For instance, the 'Meibeluxen' variety forms semi-double red blossoms. 'The Fairy' variety forms light pink blossoms having approximately 20 to 25 petals. In contrast the white blossoms of the new variety average only approximately 5 to 6 and rarely 7 petals per flower.

The new variety has been found to undergo asexual propagation in France and at Wasco, Calif., by a number of routes, including budding, grafting, and by the use of cuttings. Asexual propagation by the above-mentioned techniques in France and at Wasco, Calif., has shown that the characteristics of the new variety are stable and are strictly transmissible by such asexual propagation from one generation to another.

The new variety has been named the 'Meipadan' variety.

BRIEF DESCRIPTION OF THE PHOTOGRAPH

The accompanying photograph shows as nearly true as it is reasonably possible to make the same, in a color illustration of this character, typical specimens of the blossoms and foliage of the new variety. The rose plants of the new variety were approximately two years of age and were observed during June while growing outdoors on their own roots at West Grove, Pa.

DETAILED DESCRIPTION

The chart used in the identification of the colors is that of The Royal Horticultural Society (R.H.S. Colour Chart). The description is based on the observation of two year-old plants during June while growing outdoors on their own roots at West Grove, Pa.

Class: Shrub Rose.

Plant:

*Height.*—Approximately 40 to 60 cm on average at the end of the growing season.

*Width.*—Approximately 70 cm to 120 cm on average at the end of the growing season.

*Habit.*—Low-growing and mounded, and useful as a ground cover.

Branches:

*Color.*—Young stems: near Yellow-Green Group 143A. Adult wood: two year-old stems are close to Greyed-Green Group 191A. As a corky bark develops, the bark color varies and is primarily near and through Greyed-Orange Group 166B and 166C and Greyed-Orange Group 174A with lighter fissures of the new cork near Greyed-Orange Group 167C. A waxy coating commonly develops over the darker areas of the bark and is near and through Grey Group 201C and 201D.

*Thorns.*—Size: approximately 1 cm in length. Quantity: on 10 cm of young stems approximately 10 on average. Color: on young stems near Green Group 138B with subtle shading of Greyed-Purple Group 186D towards the base.

Leaves:

*Stipules.*—Adnate, fimbriate, approximately 1.2 to 2.7 cm in length, and approximately 4 to 9 mm in width.

*Rachis.*—Approximately 2.0 to 8.2 cm in length, near Green Group 135A on the upper surface, and near Green Group 139B on the under surface.

*Petioles.*—Approximately 1.1 to 2.2 cm in length on the terminal leaflet, approximately 1.7 to 3.0 cm in length for the other leaflets, near Green Group 135A on the upper surface, and near Green Group 139B on the under surface.

*Leaflets.*—Number: 3, 5, and 7 (most often). Shape: broadly elliptical to broadly ovate with an acute to broadly acute apex and a cuneate base. Size: the terminal leaflets commonly are approximately 5 cm in length and approximately 2.8 cm in width on average. Margins: serrate to serrulate. Texture: glabrous. General appearance: very dense, and dark green with a glossy aspect. Color (young foliage): Upper surface: near Green Group 139A. Under surface: near and through Green Group 137A and 137B. Color (adult foliage): Upper surface: near Green Group 139A. Under surface: shading towards and through Green Group 138A and Green Group 137C.

Inflorescence:

*Number of flowers.*—Commonly 1 to 5 per stem, and most commonly 3 to 5 per stem.

*Peduncle.*—Glaucous, near Green Group 143A in coloration, the length is approximately 3 cm on average, and the width is approximately 1.5 mm on average.

*Sepals.*—Number: 5. Extensions: commonly 0 to 3 foliaceous appendages per sepal. Upper surface: near Greyed-Green Group 191B and 191C at the tip and shading to Greyed-Green Group 192A at the base. Under surface: near Greyed-Green Group 141B at the tip and shading to Green Group 140A and Green Group 141D at the base.

*Buds.*—Shape: ovoid. Length: approximately 2 cm on average. Diameter: approximately 1 cm on average.

*Flower.*—Shape: flat saucer shaped. Diameter: approximately 6 to 7 cm on average. Borne: Terminally and axially. Color (when blooming): near White Group 155D with a tinge of near Red-Purple Group 69A that provides a pearl opalescent quality under some natural lighting situations and during the cooler parts of the flowering season. Fragrance: light. Lasting quality: the blossoms commonly last approximately 7 days on the plant on average. Petal number: approximately 5 to 6 on average and rarely to 7 under normal growing conditions. Petal shape: broadly ovate to obovate, the base is broadly cuneate and the tip is emarginate to broadly obtuse to nearly truncate and mucronate. Petaloids: commonly 1 to 3 per flower. Petal arrangement: Verticillate. Sepalous petals: rarely observed. Petal texture: smooth, very thin, and approaching translucent. Petal drop: good with the petals commonly detaching cleanly before drying. Stamen number: approximately 120 on average. Anthers: approximately 1.1 mm in size on average. Pollen: none observed during observations to date. Filaments: commonly 2.5 to 7.5 mm in length. Stigmas: approximately 22 on average. Styles: approximately 22 on average. Receptacle: glaucous, near Green Group 143A in coloration, and urn shaped. The length and width are each approximately 8 mm on average, and the width is approximately 5 mm on average. Hips: None observed during observations to date.

Development:

*Vegetation.*—Very strong.

*Blooming.*—Very abundant and continuous.

*Resistance to disease.*—Excellent with respect to Black Spot.

*Aptitude to bear fruit.*—None.

Plants of the new 'Meipadan' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of Shrub rose plant characterized by the following combination of characteristics:

(a) exhibits a low-growing and mounded growth habit with good vigor, (b) abundantly forms on a continuous basis attractive single white blossoms having light fragrance, (c) forms very dense dark green foliage having a glossy aspect that contrasts well with the white blossom coloration, (d) displays exceptional Black Spot resistance, and (e) is particularly well suited for growing as attractive ornamentation in the landscape;

substantially as herein shown and described.

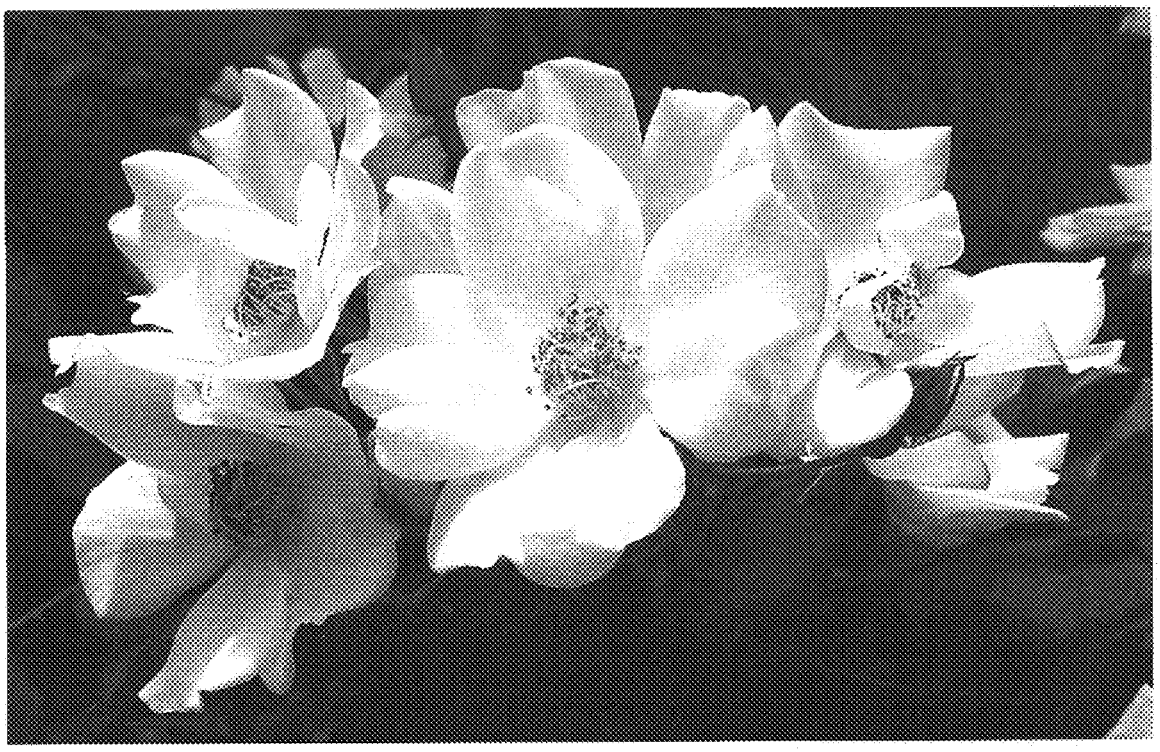

* * * * *